United States Patent
Van Engelen et al.

(10) Patent No.: US 9,617,459 B2
(45) Date of Patent: Apr. 11, 2017

(54) PLANT DERIVED CELLULOSE COMPOSITIONS FOR USE AS DRILLING MUDS

(71) Applicants: CelluComp Ltd., Fife (GB); Cosun Biobased Products B.V., Breda (NL)

(72) Inventors: Gerardus Petrus Franciscus Maria Van Engelen, Bavel (NL); Gijsbert Adriaan Van Ingen, Breda (NL); Corne Meeuwissen, Breda (NL)

(73) Assignees: Cellucomp Ltd., Fife, Scotland (GB); Cosun Biobased Products B.V., Breda (NL)

( * ) Notice: Subject to any disclaimer, the term of this patent is extended or adjusted under 35 U.S.C. 154(b) by 181 days.

(21) Appl. No.: 14/417,513

(22) PCT Filed: Jul. 26, 2013

(86) PCT No.: PCT/NL2013/050558
§ 371 (c)(1),
(2) Date: Jan. 26, 2015

(87) PCT Pub. No.: WO2014/017911
PCT Pub. Date: Jan. 30, 2014

(65) Prior Publication Data
US 2015/0203737 A1 Jul. 23, 2015

(30) Foreign Application Priority Data

Jul. 27, 2012 (EP) .................................... 12178190

(51) Int. Cl.
| | | |
|---|---|---|
| *C09K 8/10* | (2006.01) | |
| *C12P 19/02* | (2006.01) | |
| *C12P 19/14* | (2006.01) | |
| *C09K 8/20* | (2006.01) | |
| *D21C 5/00* | (2006.01) | |
| *D21C 3/02* | (2006.01) | |
| *D21C 9/00* | (2006.01) | |
| *D21H 11/18* | (2006.01) | |

(52) U.S. Cl.
CPC ................ *C09K 8/10* (2013.01); *C09K 8/206* (2013.01); *C12P 19/02* (2013.01); *C12P 19/14* (2013.01); *D21C 3/02* (2013.01); *D21C 5/00* (2013.01); *D21C 5/005* (2013.01); *D21C 9/002* (2013.01); *D21C 9/004* (2013.01); *D21C 9/007* (2013.01); *D21H 11/18* (2013.01)

(58) Field of Classification Search
None
See application file for complete search history.

(56) References Cited

U.S. PATENT DOCUMENTS

| | | |
|---|---|---|
| 4,374,702 A | 2/1983 | Turbak et al. |
| 4,378,381 A | 3/1983 | Turbak et al. |
| 4,629,575 A | 12/1986 | Weibel |
| 4,831,127 A | 5/1989 | Weibel |
| 4,923,981 A | 5/1990 | Weibel et al. |
| 5,179,076 A | 1/1993 | Elward-Berry |
| 5,252,352 A | 10/1993 | Banach et al. |
| 5,276,075 A | 1/1994 | Santini |
| 5,567,462 A | 10/1996 | Ehrlich |
| 5,656,734 A | 8/1997 | Ehrlich |
| 5,964,983 A | 10/1999 | Dinand et al. |
| 5,998,349 A | 12/1999 | Guillou |
| 6,103,790 A | 8/2000 | Cavaille et al. |
| 6,117,545 A | 9/2000 | Cavaille et al. |
| 6,129,867 A | 10/2000 | Chevalier et al. |
| 6,312,669 B1 | 11/2001 | Cantiani et al. |
| 6,348,436 B1 | 2/2002 | Langlois et al. |
| 6,703,497 B1 | 3/2004 | Ladouce et al. |
| 6,967,027 B1 | 11/2005 | Heux et al. |

(Continued)

FOREIGN PATENT DOCUMENTS

| | | |
|---|---|---|
| EP | 0 102 829 | 3/1984 |
| EP | 0 134 084 | 3/1985 |

(Continued)

OTHER PUBLICATIONS

European Search Report of EP Application No. 12178190 mailed Nov. 26, 2012.
International Search Report of PCT/NL2013/050558 mailed Aug. 29, 2013.
International Search Report of PCT/NL2013/050559 mailed Oct. 21, 2013.
International Search Report of PCT/NL2013/050560 mailed Oct. 15, 2013.
Machine Translation of JP 2008-179666, filed Aug. 7, 2008.
Dinand et al., "Parenchymal cell cellulose from sugar beet pulp: preparation and properties", Cellulose, 1996, vol. 3, pp. 183-188.
Machine translation of JP 2008-179666, 2016.

(Continued)

*Primary Examiner* — John J Figueroa
(74) *Attorney, Agent, or Firm* — Gilberto M. Villacorta; Sunit Talapatra; Foley & Lardner LLP

(57) ABSTRACT

This invention relates to water-based well drilling fluids. It has been found that cellulose based particles, which comprise cell wall material and their networks of cellulose based fibers and nanofibrils can be used to produce suspensions having viscosity and rheological properties particularly suitable for use as a drilling fluid. It is assumed that the organization of the cellulose fibrils, as it exists in the parenchymal cell walls, is at least partly retained in the cellulose based particles of the invention, even though part of the pectin and hemicellulose is removed there from. Breaking plant-based pulp down into this kind of cellulose based particles involves fewer and gentler processes than to break the pulp down further into cellulose nanofibrils, and therefore the present cellulose based particles can be produced much faster and at lower cost than completely unraveled cellulose nanofibrils. The well drilling fluids based on the cellulose material of this invention are stable over a wide range of operating temperatures.

17 Claims, No Drawings

(56) References Cited

U.S. PATENT DOCUMENTS

| | | |
|---|---|---|
| 7,705,084 B2 | 4/2010 | Van De Mark et al. |
| 7,776,807 B2 | 8/2010 | Canto et al. |
| 8,153,707 B2 | 4/2012 | Lynch et al. |
| 2004/0086626 A1 | 5/2004 | Lundberg et al. |
| 2005/0074542 A1 | 4/2005 | Lundberg et al. |
| 2005/0256262 A1 | 11/2005 | Hill et al. |
| 2006/0102869 A1 | 5/2006 | Cavaille et al. |
| 2006/0289132 A1 | 12/2006 | Heijnesson-Hulten |
| 2008/0108541 A1 | 5/2008 | Swazey |
| 2008/0146485 A1 | 6/2008 | Swazey |
| 2008/0146701 A1 | 6/2008 | Sain et al. |
| 2009/0269376 A1 | 10/2009 | Lundberg et al. |
| 2012/0142909 A1 | 6/2012 | Lundberg |
| 2014/0124150 A1 | 5/2014 | Sabourin et al. |
| 2015/0191612 A1* | 7/2015 | Van Engelen ............ C09D 5/00 524/35 |
| 2015/0203737 A1 | 7/2015 | Van Engelen et al. |
| 2015/0210957 A1 | 7/2015 | Napolitano |
| 2015/0210967 A1* | 7/2015 | Van Engelen ......... C11D 3/382 510/418 |
| 2016/0030907 A1* | 2/2016 | Van Engelen .......... C12P 19/14 435/277 |

FOREIGN PATENT DOCUMENTS

| | | |
|---|---|---|
| JP | 2008-179666 A | 8/2008 |
| WO | WO-2009/101545 | 8/2009 |
| WO | WO-2010/105847 A1 | 9/2010 |
| WO | WO-2012/003307 A2 | 1/2012 |
| WO | WO-2012/052306 A1 | 4/2012 |
| WO | WO-2012/065924 | 5/2012 |
| WO | WO-2012/065925 | 5/2012 |
| WO | WO 2013/128196 A1 | 9/2013 |

\* cited by examiner

PLANT DERIVED CELLULOSE COMPOSITIONS FOR USE AS DRILLING MUDS

CROSS-REFERENCE TO RELATED APPLICATIONS

This application is the National Phase of International Patent Application No. PCT/NL2013/050558, filed Jul. 26, 2013, published as WO 2014/017911, which claims priority to European Application No. 12178190.0, filed Jul. 27, 2012. The contents of this application is herein incorporated by reference in its entirety.

FIELD OF THE INVENTION

This invention relates to water-based well drilling fluids, which display rheological stability throughout a wide temperature range.

BACKGROUND OF THE INVENTION

It is well known in the art to use rheology modifiers in drilling fluids when drilling wells, such as in the oil and gas industry. Such fluids, or "muds," serve several functions in the drilling process, including: removal of drilled cuttings, suspension of high specific gravity weight material and fine cuttings, sealing of the sides of the wellbore so as to minimize drilling fluid loss into the formation, provision of a hydrostatic head to prevent blowouts from high pressure fluids into the wellbore or up through the wellbore to the surface, creation of a low-friction surface on the wellbore to facilitate rotation and removal of the drill string as operational conditions require, cooling of the drill bit and lubrication to prevent the drill pipe from sticking during rotation.

An excellent background document summarizing the composition and use of drilling fluids is Remont, Larry J.; Rehm, William A.; McDonald, William M.; and Maurer, William C., "Evaluation of Commercially Available Geothermal Drilling Fluids," issued by Sandia Laboratories, operated for the United States Energy Research and Development Administration (Nov. 1, 1976) (hereinafter referred to as "Remont et al.").

Drilling muds traditionally are colloidal suspensions of clays and/or minerals, in either oil or water. Various chemicals can be added to alter, enhance, influence or modify the properties of the suspension, as is well known in the art. For example, a weighting agent, such as barium sulfate, or "barite," may be added to increase the density of the mud. Viscosifiers may be used to increase viscosity and gel strength. Deflocculants, such as lignosulfonates, prevent formation of clay particles. Filtration control materials, such as soluble polymers or starch, are added to encourage the development of the filter cake on the sides of the wellbore so that a minimal amount of the drilling fluid will enter a permeable formation.

The search for oil and gas has led to the drilling of deeper wells in recent years. Because of the temperature gradient in the earth's crust, deeper wells have higher bottomhole temperatures.

It is therefore broadly recognized in the art that there is a need for a drilling fluid which retains rheological stability throughout a broad temperature range for efficient drilling of these deeper wells.

Because of their better thermal stability, oil-based fluids typically have been used in high temperature applications. However, due to the environmental impact of the disposal of these spent slurries, and the drilled cuttings carried in these slurries, water-based fluids have become more and more the fluid of choice in the industry. Water-based fluids are also preferable in high pressure applications, such as deep wells, because oil-based fluids are more compressible than water-based fluids. This increased compressibility results in increased viscosity.

For a mud to work well in high temperature bottomhole conditions, it must be rheologically stable over the entire range of temperatures to which it will be exposed. This range is generally from ambient temperature to bottomhole temperature. The rheological stability of a mud is monitored by measuring its yield point and gel strengths, in accordance with standard drilling fluid tests, before and after circulation down the wellbore. These standard tests, which include the tests for yield point and gel strengths, are well known in the industry and are described in "Recommended Practice Standard Procedure for Field Testing Water-Based Drilling Fluids," Recommended Practice 13B-1 (1st ed. Jun. 1, 1990), American Petroleum Institute (hereinafter referred to as "RP 13B-1").

The prior art has several partial solutions to the difficulties encountered at high temperature operation. One such solution includes the use of polymers instead of clay as viscosifiers. At present, guar gum is typically applied for this purpose in practice. These polymers however are not satisfactory in applications above approximately 120° C.

EP 0 134 084 discloses well drilling fluids based on parenchymal cell cellulose. This material is obtained by the process described in EP 0 102 829, teaching a process characterized by hydrolysis of plant pulp in either strong acid or strong base at high temperatures for short periods in adjunct with mechanical shearing to yield cellulosic and hemicellulosic biopolymers without excessive degradation thereof. A typical process comprises the steps of suspending the sugar beet pulp in an acidic (pH<4.5) or alkaline (pH>10.0) aqueous medium; heating the suspension to a temperature of more than 125° C. (0.5 MPa); keeping the suspension at a temperature of more than 125° C. for a period of between 15 seconds and 360 seconds; subjecting the heated suspension to mechanical shearing in a tube reactor followed by rapid depressurization through small orifices into a zone which is at atmospheric pressure; filtering the suspension and recovering the insoluble fraction which contains the parenchyma cellulose and the soluble fraction (filtrate) which contains the hemicelluloses; treating the cellulose fraction by bleaching with sodium hypochlorite and mechanical defibrillation to produce a parenchyma cellulose paste constituted by cell wall fragments. It is evident from EP 0 134 084 that, although the materials in principle have adequate properties for use in well drilling in general, they are not suitable for use in drilling operation involving very high temperatures, e.g. in excess of 160° C. or 175° C., conditions which are becoming increasingly common in oil well drilling, as explained above.

U.S. Pat. No. 6,348,436 addresses this shortcoming of the EP 0 134 084/EP 0 102 829 materials. According to U.S. Pat. No. 6,348,436, cellulose nanofibrils are used, containing a certain percentage of the non cellulosic acidic polysaccharides retained at the surface of the nanofirbrils having the effect of preventing them from associating with each other. These nanfibrils are obtained by the process described in detail in U.S. Pat. No. 5,964,983. This process comprises the steps of hydrolysing sugar beet pulp at a moderate temperature of 60-100° C., at least one extraction with a base having a concentration of less than 9 wt. % and homogenisation at high pressure and high temperature. This process results in the unraveling of the nanofibrils without breaking them. Electron-microscope observation of these materials indicated that the average cross-section of the nanofibrils was 2-4 nm and the nanofibrils have a length of up to 15-20 µm long.

The reduction of plant fibers to the individual cells, and of plant cells to cellulose fibers and nanofibrils is an energetically intense process, requiring chemical and mechanical action on the plant cells.

Nanofibrililated cellulose materials, furthermore, are notoriously difficult to handle. Systems of unravelled cellulose nanofibrils produce gels at a solids content of not more than 1-2 wt. % in water. Upon concentrating such compositions to higher dry solids amounts, these systems tend to collapse resulting in agglomeration of the nanofibrils. In order to produce fluids having suitable rheological properties from these concentrated nanofibrilated materials again, if possible at all, intensive treatment is required, e.g. by strong agitation. This is a serious draw-back with a view to well drilling applications, where significant amounts of drilling fluids are consumed, which implies that either relatively large volumes (of water) would have to be stored and transported or large amounts of materials would have to undergo intensive treatment at the well drilling site. Not surprisingly, substantive R&D efforts in this field, so far, have not resulted in the actual commercial use of nanofibrilated cellulose materials in well drilling.

Thus, there still remains a need for a well drilling fluid material that is convenient and economical to produce on a large scale and can be used in drilling operations involving high temperatures, such as above 175° C. or 180° C.

SUMMARY OF THE INVENTION

Surprisingly, the inventors have found that cellulose based particles, which comprise cell wall material and their networks of cellulose based fibers and nanofibrils can be used to produce suspensions having viscosity and rheological properties particularly suitable for use as a drilling fluid. Breaking plant-based pulp down into this kind of cellulose based particles involves fewer and gentler processes than to break the pulp down further into cellulose nanofibrils, and therefore the present cellulose based particles can be produced much faster and at lower cost than completely unraveled cellulose nanofibrils. Surprisingly, well drilling muds can be produced using these particulate cellulose based materials, possessing rheological characteristics and, in particular, heat stability, at least as good as the prior art well drilling muds based on cellulose nanofibrils. Thus, by retaining cellulose in the form of particles comprising sections of plant cell walls rather than entirely breaking cellulose down to individual nanofibrils, advantageous properties of the material can be retained whilst production time and energy consumption can be reduced.

Once compositions comprising the cellulose species have been produced, it is often desirable to increase the concentration of the cellulose species to reduce the volume of the material and thereby reduce storage and transport costs. The inventors have found that aqueous dispersions of the particulate cellulose material of the invention can suitably be concentrated to a dry matter content of at least 10 wt. %, e.g. up to 25 wt. %, to give a product that is still easily (re)dispersible in water to obtain cellulose contents desirable for well-drilling applications.

Without wishing to be bound by any particular theory, it is assumed that the organization of the cellulose fibrils, as it exists in the parenchymal cell walls, is at least partly retained in the cellulose based particles of the invention, even though part of the pectin and hemicellulose is removed there from. Hence, contrary to the above-described prior art the cellulose based nanofibrils are not completely unraveled, i.e. the material is not primarily based on completely unraveled nanofibrils, but instead can be considered to comprise, as the main constituent, parenchymal cell wall debris, having substantial parts of the pectin and hemicellulose removed. The inventors hypothesize that at least some hemicellulose is to be retained in the material to support the structural organization of the cellulose in the particles, e.g. by providing an additional network. Such hemicellulose networks would hold the cellulose fibers together, thereby providing structural integrity and strength to the cellulose particle.

The present invention provides the new particulate cellulose based material as well as its production and use in well drilling.

DETAILED DESCRIPTION OF THE INVENTION

Hence, an aspect of the invention, concerns a parenchymal cellulose composition comprising a particulate cellulose material containing, by dry weight of the particulate cellulose material, at least 70% cellulose, less than 10% pectin and at least 3% hemicellulose, wherein the particulate material has a volume-weighted median major particle dimension within the range of 25-75 µm, preferably within the range of 35-65 µm, as measured by laser light diffractometry.

The term "cellulose" as used herein refers to homogeneous long chain polysaccharides comprised of β-D-glucose monomer units, of formula $(C_6H_{10}O_5)_n$, and derivatives thereof, usually found in plant cell walls in combination with lignin and any hemicellulose. The parenchymal cellulose of this invention may be obtained from a variety of plant sources containing parenchymal cell walls. Parenchymal cell wall, which may also be denoted as 'primary cell wall', refers to the soft or succulent tissue, which is the most abundant cell wall type in edible plants. The basic process of the invention may be generally described as providing novel and improved fiber waste by-product from citrus fruit pulp or fiber from sugar beet, tomatoes, chicory, potatoes, pineapple, apple, cranberries, grapes, carrots and the like (exclusive of the stems, and leaves). For instance, in sugar beets, the parenchyma cells are the most abundant tissue surrounding the secondary vascular tissues. Parenchymal cell walls contain relatively thin cell walls (compared to secondary cell walls) which are tied together by pectin. Secondary cell walls, are much thicker than parenchymal cells and are linked together with lignin. This terminology is well understood in the art. The parenchymal cellulose in accordance with the invention is preferably obtained from sugar beet, potato, carrot and citrus. In a particularly preferred embodiment of the invention, the parenchymal cellulose is obtained from sugar beet, e.g. as a by-product of sucrose production.

The particulate cellulose material of this invention contains particles of specific structure, shape and size, as explained herein before. Typically the material contains particles having the form of platelets comprising parenchymal cellulose structures or networks. It is preferred that the size distribution of the particulate material falls within certain limits. When the distribution is measured with a laser light scattering particle size analyzer, such as the Malvern Mastersizer or another instrument of equal or better sensitivity, the diameter data is preferably reported as a volume distribution. Thus the reported median for a population of particles will be volume-weighted, with about one-half of the particles, on a volume basis, having diameters less than the median diameter for the population. Typically, the median major dimension of the particles of the parenchymal cellulose composition is within the range of 25-75 µm. More preferably the median major dimension of the particles of the parenchymal cellulose composition is within the range of 35-65 µm. Typically at least about 90%, on a volume basis, of the particles has a diameter less than about 120 µm, more preferably less than 110 µm, more preferably less than 100 µm. Preferably, the particulate cellulose material has a volume-weighted median minor dimension larger than 0.5 µm, preferably larger than 1 µm.

The compositions of this invention are characterized by the fact that the majority of the cellulose material is present in the form of particles that are distinct from the nanofibrilised cellulose described in the prior art in that the cellulose nanofibrils are not substantially unraveled, as discussed before. Preferably, less than 10%, or more preferably less than 1% or less than 0.1% by dry weight of the cellulose within the composition is in the form of nanofibrillated cellulose. This is advantageous as nanofibrillated cellulose negatively affects the redispersability of the material, as indicated herein before. By 'nanofibrils' we refer to the fibrils making up the cellulose fibers, typically having a width in the nanometer range and a length of between up to 20 µm. The nomenclature used in the field over the past decades has been somewhat inconsistent in that the terms 'microfibril' and 'nanofibril' have been used to denote the same material. In the context of this invention, the two terms are deemed to be fully interchangeable.

In accordance with the invention, the plant parenchymal cellulose material has been treated, modified and/or some components may have been removed but the cellulose at no time has been broken down to individual microfibrils, thereby losing the structure of plant cell wall sections. As mentioned before, the cellulose material of this invention has a reduced pectin content, as compared to the parenchymal cell wall material from which it is derived. Removal of some of the pectin is believed to result in enhanced thermal stability. The term "pectin" as used herein refers to a class of plant cell-wall heterogeneous polysaccharides that can be extracted by treatment with acids and chelating agents. Typically, 70-80% of pectin is found as a linear chain of α-(1-4)-linked D-galacturonic acid monomers. The smaller RG-I fraction of pectin is comprised of alternating (1-4)-linked galacturonic acid and (1-2)-linked L-rhamnose, with substantial arabinogalactan branching emanating from the L-rhamnose residue. Other monosaccharides, such as D-fucose, D-xylose, apiose, aceric acid, Kdo, Dha, 2-O-methyl-D-fucose, and 2-O-methyl-D-xylose, are found either in the RG-II pectin fraction (<2%), or as minor constituents in the RG-I fraction. Proportions of each of the monosaccharides in relation to D-galacturonic acid vary depending on the individual plant and its micro-environment, the species, and time during the growth cycle. For the same reasons, the homogalacturonan and RG-I fractions can differ widely in their content of methyl esters on GalA residues, and the content of acetyl residue esters on the C-2 and C-3 positions of GalA and neutral sugars. It is preferred that the particulate cellulose material of the invention comprises less than 5 wt. % of pectin, by dry weight of the particulate cellulose material, more preferably less than 2.5 wt. %. The presence of at least some pectin in the cellulose material is nevertheless desired. Without wishing to be bound by any theory it is assumed that pectin plays a role in the electrostatic interactions between particles contained in the material and/or in supporting the network/structure of the cellulose. Hence, it is preferred that the particulate cellulose material contains at least 0.5 wt % of pectin by dry weight of the particulate cellulose material, more preferably at least than 1 wt. %.

As mentioned before, the cellulose material of this invention has a certain minimum content of hemicellulose. The term "hemicellulose" refers to a class of plant cell-wall polysaccharides that can be any of several homo- or heteropolymers. Typical examples thereof include xylane, arabinane xyloglucan, arabinoxylan, arabinogalactan, glucuronoxylan, glucomannan and galactomannan. Monomeric components of hemicellulose include, but are not limited to: D-galactose, L-galactose, D-mannose, L-rhamnose, L-fucose, D-xylose, L-arabinose, and D-glucuronic acid. This class of polysaccharides is found in almost all cell walls along with cellulose. Hemicellulose is lower in weight than cellulose and cannot be extracted by hot water or chelating agents, but can be extracted by aqueous alkali. Polymeric chains of hemicellulose bind pectin and cellulose in a network of cross-linked fibers forming the cell walls of most plant cells. Without wishing to be bound by any theory, it is assumed that the presence of at least some hemicellulose is important to the structural organization of the fibers making up the particulate material. Preferably the particulate cellulose material comprises, by dry weight of the particulate cellulose material, 1-15 wt % hemicellulose, more preferably 1-10 wt % hemicellulose, most preferably 1-5 wt % hemicellulose.

The parenchymal cellulose composition of this invention typically can comprise other materials besides the particulate cellulose material, as will be understood by those skilled in the art. Such other materials can include, e.g., remnants from (the processing of) the raw plant cell wall source (other than the particulate cellulose material of the invention) and any sort of additive, excipient, carrier material, etc., added with a view to the form, appearance and/or intended application of the composition.

The compositions of this invention, typically may take the form of an aqueous suspension or pasta like material comprising dispersed therein the particulate cellulose material of this invention. In an embodiment, an aqueous soft solid like dispersion is provided comprising at least 10% particulate cellulose material solids content. The composition may comprise at least 20% particulate cellulose material solids content. The composition may comprise at least 30% particulate cellulose material solids content. In the context of this invention, these concentrated dispersions may also be referred to as the 'well drilling fluid additive'. These additives may be added in small quantities to aqueous media to produce a well-drilling fluid.

In an embodiment if the invention, a surfactant or dispersant may be incorporated in this well-drilling fluid additive. The surfactant or dispersant may interact with the particulate cellulose based material within the composition and inhibit formation or inter-platelet bonds being formed and therefore inhibit aggregation of the cellulose based particles. The surfactant or dispersant may be Span 20, for example.

A parenchymal cellulose material as described here above can be obtained using a specific process, which process involves a step of mild alkali treatment to hydrolyse the cell wall material followed by an intense homogenization process which does however not result in the complete unraveling of the material to its individual nanofibrils.

Accordingly, an aspect of the invention concerns a method of preparing a parenchymal cellulose composition as described in the foregoing, said method comprising the steps of;
a) providing a vegetable pulp;
b) subjecting the vegetable pulp to chemical and/or enzymatic treatment resulting in partial degradation and/or extraction of pectin and hemicellulose, wherein the mixture is homogenized once or several times by applying low shear force during and/or after said chemical and/or enzymatic treatment;
c) subjecting the material resulting from step b) to a high shear process, wherein the particle size of the cellulose material is reduced so as to yield a particulate material having a volume-weighted median major dimension within the range of 25-75 μm, as measured by laser diffractiometry;
d) removing liquid from the mass obtained In step c).

The vegetable pulp used as the starting material typically comprises an aqueous slurry comprising pectin-containing plant materials, such as citrus peels, sugar beet pulp, sunflower residues, pomace residues, etc. Particularly preferred is the use of fresh, pressed-out sugar beet pulp from which the sugars have been extracted and which has a dry solids content of 10-50 wt. %, preferably 20-30 wt. %, for example approximately 25 wt. %. Sugar beet pulp is the production residuum from the sugar beet industry. More specifically, sugar beet pulp is the residue from the sugar beet after the extraction of sucrose there from. Sugar beet processors usually dry the pulp. The dry sugar beet pulp can be referred to as "sugar beet shreds". Additionally, the dry sugar beet pulp or shreds can be formed and compressed to produce "sugar beet pellets". These materials may all be used as the starting material, in which case step a) will comprise suspending the dry sugar beet pulp material in an aqueous liquid, typically to the afore-mentioned dry solids contents. Preferably however, fresh wet sugar beet pulp is used as the staring material.

Another preferred starting material is ensilaged sugar beet pulp. As used herein, the term "ensilage" refers to the conservation in a moist state of vegetable materials as a result of acidification caused by anaerobic fermentation of carbohydrates present in the materials being treated. Ensilage is carried out according to known methods with pulps preferably containing 15 to 35% of dry matter. Ensilage of sugar beets is continued until the pH is at least less than about 5 and greater than about 3.5. (see U.S. Pat. No. 6,074,856). It is known that pressed beet pulps may be ensilaged to protect them from unwanted decomposition. This process is most commonly used to protect this perishable product, the other alternative being drying to 90% dry matter. This drying has the disadvantage of being very energy-intensive. The fermentation process starts spontaneously under anaerobic conditions with the lactic acid bacteria present. These microorganisms convert the residual sucrose of the pressed beet pulp to lactic acid, causing a fall in the pH and hence maintaining the structure of the beet pulp.

In an embodiment of the invention the vegetable pulp is washed in a flotation washer before the chemical or enzymatic treatment is carried out, in order to remove sand and clay particles and, in case ensilaged sugar beet pulp is used as a starting material, in order to remove soluble acids.

In accordance with the invention, the chemical and/or enzymatic treatment results in the degradation and/or extraction of at least a part of the pectin and hemicelluloses present in the vegetable pulp, typically to monosaccharides, disaccharides and/or oligosaccharides. However, as indicated above, the presence of at least some non-degraded pectin, such as at least 0.5 wt %, and some non-degraded hemicellulose, such as 1-15 wt %, is preferred. Hence, step b) typically comprises partial degradation and/or extraction of the pectin and hemicellulose, preferably to the extent that at least 0.5 wt. % of pectin and at least 1 wt. % of hemicellulose remain. It is within the routine capabilities of those skilled in the art to determine the proper combinations of reaction conditions and time to accomplish this.

The term monosaccharide as used herein has its normal scientific meaning and refers to a monomeric carbohydrate unit. The term disaccharide as used herein has its normal scientific meaning and refers to a carbohydrate of two covalently bound monosaccharides. The term oligosaccharide as used herein has its normal scientific meaning and refers to a carbohydrate of three to ten covalently bound monosaccharides.

Preferably, the chemical treatment as mentioned in step b) of the above mentioned method comprises:
i) mixing the vegetable material pulp with a 0.1-1.0 M alkaline metal hydroxide, preferably 0.3-0.7 M alkaline metal hydroxide; and
ii) heating the mixture of vegetable material pulp and alkaline metal hydroxide to a temperature within the range of 80-120° C. for a period of at least 10 minutes, preferably at least 20 minutes, more preferably at least 30 minutes.

It has been found that the use of alkaline metal hydroxides, especially sodium hydroxide, in the above method, is necessary to remove pectin and hemicelluloses from the cellulose to the desired extent. The alkaline metal hydroxide may be sodium hydroxide. The alkaline metal hydroxide may be potassium hydroxide. The alkaline metal hydroxide may be at a concentration of at least 0.2 M, at least 0.3 M, or at least 0.4 M. The alkaline metal hydroxide, preferably is at less than 0.9 M, less than 0.8 M, less than 0.7 M or less than 0.6 M.

The use of relatively low temperatures in the present chemical process allows the vegetable material pulp to be processed with the use of less energy and therefore at a lower cost than methods known in the art employing higher temperatures. In addition, use of low temperatures and pressures ensures that minimum cellulose nanofibers are produced. Cellulose nanofibers affect the viscosity of the composition and make it more difficult to rehydrate the composition after dehydration. The vegetable material pulp may be heated to at least 80° C. Preferably, the vegetable material pulp is heated to at least 90° C. Preferably, the vegetable material pulp is heated to less than 120° C., preferably less than 100° C. As will be appreciated by those skilled in the art, the use of higher temperatures, within the indicated ranges, will reduce the processing times and vice versa. It is a matter of routine optimization to find the proper set of conditions in a given situation. As mentioned above, the heating temperature is typically in the range of 80-120° C. for at least 10 minutes, preferably at least 20 minutes, more preferably at least 30 minutes. If the heating temperature in step ii) is between 80-100° C., the heating time may be at least 120 minutes. Preferably, step ii) comprises heating the mixture to a temperature of 90-100° C. for 120-240 minutes, for example to a temperature of approximately 95° C. for about 180 minutes. In another embodiment of the invention, the mixture is heated above 100° C., in which case the heating time can be considerably shorter. In a preferred embodiment of the present invention step ii) comprises heating the mixture to a temperature of 110-120° C. for 10-50 minutes, preferably 10-30 minutes.

Alternatively or additionally, at least a part of the pectin and hemicelluloses may be degraded by treatment of the vegetable pulp with suitable enzymes. Preferably, a combination of enzymes is used, although it may also be possible to enrich the enzyme preparation with one or more specific enzymes to get an optimum result. Generally an enzyme combination is used with a low cellulase activity relative to the pectinolytic and hemicellulolytic activity. In a preferred embodiment of the present invention such a combination of enzymes, has the following activities, expressed as percentage of the total activity of the combination:

cellulase activity of 0-10%;
pectinolytic activity of 50-80%; and
hemicellulase activity of at least 20-40%

The enzyme treatments are generally carried out under mild conditions, e.g. at pH 3.5-5 and at 35-50° C., typically for 16-48 hours, using an enzyme activity of e.g. 65,000-150,000 units/kg substrate (dry matter). It is within the routine capabilities of those skilled in the art to determine the proper combinations of parameters to accomplish the desired rate and extent of pectin and hemicellulose degradation.

Before, during or after step b) the mixture is homogenized once or several times by applying low shear force. Low shear force can be applied using standard methods and equipment known to those skilled in the art, such as conventional mixers or blenders. Preferably, the step of homogenisation at low shear is carried out for at least 5 minutes, preferably at least 10 minutes, preferably at least 20 minutes. Typically low shear mixing is done at least once during step b), preferably at least twice, more preferably at least three times. In a preferred embodiment of the invention low shear mixing is performed, for at least one fourth of the total duration of step b), preferably at least one third of the total time of step b), more preferably at least half the time. It has been found that it is advantageous to homogenise at low shear at this stage, as it helps breaking the pulp down into individual cells, which are then in turn, during the treatment of step c), broken up into cellulose platelets.

Step c) typically involves high shear treatment of the mass resulting from step b), which will typically result in cellulose platelets being e.g. less than half the size of the parent cells, preferably less than one third the size of the parent cells. As mentioned before, the inventors have found that it is important to retain part of the structure in the cellulose particles to ensure that the composition provides the advantageous characteristics described herein. As will be understood from the foregoing, the processing during step d) should not result in the complete or substantial unraveling to nanofibrils.

The process of obtaining the desired particle size characteristics of the cellulose material in step c) is not particularly limited and many suitable methods are known to those skilled in the art. Examples of suitable size reducing techniques include grinding, crushing or microfluidization. Examples of useful separation techniques are sieve classification, use of cyclones and centrifugation. These methods may be used alone, or otherwise two or more of them may be combined. Preferably, the particle size of the cellulose is reduced before a separation on the basis of particle size is carried out. Suitably, the process is conducted as wet processes, typically by subjecting the aqueous liquid from step b), which may e.g. contain 1 to 50% cellulosic material, to grinding, crushing, or the like, known in the art. Preferred grinding methods include: grinding using stirring blades such as unidirectional rotary-, multi-axis rotary-, reciprocal inverse-, vertical motion-, rotary and vertical motion-, and duct line-system stirring blades, such as portable mixers, solid mixers, and lateral mixers; jet-system stirring grinding using e.g. line mixers; grinding using high-shear homogenizers, high-pressure homogenizers, ultrasonic homogenizers, and the like; rotary extrusion-system grinding using kneaders; and grinding combining consolidation with shearing, such as roll mills, ball mills, vibratory ball mills, and bead mills. These methods may be used alone or in combination. A suitable crushing method includes screen system crushing using e.g. screen mills and hammer mills; blade rotating shear screen system crushing using e.g. flash mills; air jet system crushing using e.g. jet mills; crushing combining consolidation with shearing, using e.g. roll mills, ball mills, vibratory ball mills, and bead mills; and a stirring blade system crushing method. These methods may be used alone or in combination. Most preferred examples of high shear equipment for use in step c) include friction grinders, such as the Masuko supermasscolloider; high pressure homogenizers, such as a Gaulin homogeninizer, high shear mixers, such as the Silverson type FX; in line homogenizer, such as the Silverson or Supraton in line homogenizer; and microfluidizers. The use of this equipment in order to obtain the particle properties required by this invention is a matter of routine for those skilled in the art.

In a preferred embodiment of the invention, heating is discontinued after step c) and the mass may be allowed to cool in between steps c) and d) or it may be transferred to the homogenizer directly, where no additional heating takes place. In a preferred embodiment step c) is performed at ambient temperature.

The aim of the removal of water during step d) may be twofold. On the one hand, the removal of water allows for the removal of a substantial fraction of dissolved organic material as well as a fraction of unwanted dispersed organic matter, i.e. having a particle size well below the particle size range of the particulate cellulose material. On the other hand, it is preferable that the dry solids content of cellulose in the composition is above a certain minimal level for practical reasons.

In view of the first objective, it is preferred not to use methods relying on evaporation, as will be understood, since this will not remove any of the dissolved salts, pectin, proteins, etc., which are exactly the components to be washed out by this step. Preferably, step d) does not comprise a drying step, such as evaporation, vacuum drying, freeze-drying, spray-drying, etc. In one preferred embodiment of the invention, the mass may be subjected to microfiltration, dialysis, centrifuge decantation or pressing.

In a particularly preferred embodiment of the invention, step d) comprises pressing of the composition, while allowing the composition to expand laterally, to reduce the water content of the composition. It has been found that allowing the composition to expand laterally whilst being pressed allows the cellulose platelets within the composition to be reoriented such that the structure of the cellulose platelets is not damaged or changed during pressing at the first pressure. It is believed that this ensures that the composition may be re-dispersed readily within an aqueous medium after pressing. The mixture of step c) may be pressed to a concentration of more than 10% solids. Preferably, step d) comprises pressing the composition, while allowing the composition to expand laterally, at a first pressure for a period of at least ten minutes; and then pressing the composition at a second, higher pressure to further reduce the water content of the composition. Preferably, the first pressure at which the composition is pressed is less than 2 kg/cm2. The first pressure at which the composition is pressed may be less than 1.5 kg/cm2. The composition may be pressed to a sheet of thickness of less than 5 mm. Preferably, the composition is pressed to a thickness of less than 2 mm.

As will be understood by those skilled in the art, it is possible to incorporate multiple processing steps in order to achieve optimal results. For example, an embodiment is envisaged wherein step d) additionally comprises subjecting the mixture to microfiltration, dialysis, centrifuge decantation, etc. followed by a step of pressing the composition, while allowing the composition to expand laterally, as described above.

Preferably, following step d), the composition is added to an aqueous medium and the cellulose particles within the composition are rehydrated and uniformly suspended within the aqueous medium under low shear mixing. Rehydration under low shear mixing ensures that the energy cost to rehydrate is low and that the cellulose platelets are not damaged, or that a significant proportion of the cellulose platelets are not damaged during the mixing process.

Once compositions comprising the cellulose species have been produced, it is often desirable to increase the concentration of the cellulose species to reduce the volume of the composition and thereby reduce storage and transport costs. Accordingly, the method of the present aspect of the invention produces a composition of cellulose platelets that is concentrated to at least 5 wt %, preferably at least 10 wt %, solids that may be then be added in small quantities to aqueous media to modify the properties of said media. The high concentration of the composition allows the composition to occupy a smaller volume than other such compositions, and therefore reduces the costs for storage and transportation of the composition.

As mentioned before, the composition can be re-dispersed into aqueous media with low shear mixing. For example, the composition may be rehydrated and re-dispersed into aqueous media using a stirrer with paddles rotating with a tip speed of 1.3 m/s, to give a well drilling fluid according to this invention.

Hence, a further aspect of the present invention concerns well drilling fluid comprising an aqueous medium and a parenchymal cellulose composition according to any one preceding claim dispersed in said aqueous medium.

It should be noted that the viscosifying effect and or the heat resistance of the parenchymal cellulose composition according to the invention constitutes a significant improvement over that of the polysaccharides currently used in practice. In a preferred embodiment of the invention a well drilling fluid as defined herein is provided, wherein the well drilling fluid is characterized by its ability to maintain a stable viscosity of at least 40 resp. 90 for at least 16 hours, at a temperature of 175° C., as measured by Fann reading at 100 rpm using 2 resp 3.5 ppb (pounds per barrel=g/350 ml).

The content of parenchymal cellulose in the drilling fluid can vary within a wide range. However, it is advantageously between 0.05 and 2% relative to the total weight of the fluid, and preferably between 0.05 and 1%.

Besides the parenchymal cellulose composition, the well drilling fluid according to the invention can comprise one or more conventional well-drilling additives, as will be understood by those skilled in the art. Such additives are added to provide various specific functional characteristics. Some common additives include thinning or dispersing agents, lubricants, shale stabilizing agents, pH control agents, filtrate reducing agents, fluid loss agents, corrosion inhibitors, oxygen scavengers, and weighting agents.

Dispersants/deflocculants or thinners known for use in the oil industry can be e.g. lignite, causticized lignite, causticized potassium lignite, chrome lignite, chrome lignosulfonate, ferrochrome lignosulfonate, chrome-free lignosulfonate, tannin and modified chrome tannin, low molecular weight polyacrylates, sodium tetraphosphate, sodium pyrophosphate, and sulfonated synthetic polymers. Examples of suitable lubricants include glycols, asphalts, esters and blends thereof. Exemplary shale stabilizing agents include partially hydrolyzed polyacrylamides (PHPAs), potassium chloride, potassium acetate, potassium carbonate, potassium hydroxide, sulfonated asphalt, blown asphalt, gilsonite, polyglycols, poly amino acids, surfactants, cationic polymers and mixed metal hydroxide (MMH). Exemplary Oxygen scavenger can be, for example, hydroxylamines, hydrazine, sulphites, bisulphites, hydrosulphites and borohydrides. Examples of corrosion inhibitors are amine-based or inorganic thiocyanate-base additives. Fluid loss agents include water-soluble or water-swellable polymers, such as cellulose ethers (CMC, PAC, HEC, CMHEC, cationic CMC), starch and its derivatives, guar gum and its derivatives, xanthan gums, resins, resinated lignite, synthetic polymers and copolymers of acrylamide, acrylic acid, 2-acrylamido-2-methylpropanesulfonic acid (AMPS), and polyglycols. Filtrate-reducing agents can be, for example, cellulosic compounds, polyacrylamides, high molecular weight polyacrylates, succinoglycans, native starch or its derivatives and charcoal. Weighting agents are conventionally chosen from alkaline-earth metal sulphates, silicates or carbonates, for instance barium sulphate, calcium carbonate and potassium and sodium silicates. Examples of pH control agents for use in drilling fluids are sodium hydroxide, magnesium oxide, sodium bicarbonate, calcium oxide, potassium hydroxide, and mixtures thereof.

Depending upon the nature of the drilled formation and the selected mud composition, many other functional additives may be added to the drilling fluid to fulfill particular functions.

The amounts in which any one of these additives is to be used will depend on the particular technical requirements and desired performance properties in a given application. Choosing the appropriate additives and amounts for a given application is a routine task for one skilled in the art.

As has been mentioned in the preceding text, the parenchymal celulose composition according to the present invention is particularly suitable for use in well drilling operations, where it is used as a drilling fluid or 'drilling mud'. In this respect, any type of drilling can be suitable, whether it be vertical, horizontal or slant drilling, such as those which are performed on off-shore platforms. Furthermore the use of the present parenchymal cellulose composition as a fracturing fluid is envisaged.

Hence, an aspect of the invention concerns the use of the parenchymal cellulose material as defined in any of the foregoing as viscosifying agent in well-drilling fluids or drilling muds, especially in oil well drilling. Furthermore, an aspect of the invention concerns the use of the parenchymal cellulose material as defined in any of the foregoing as viscosifying agent in fracturing fluids.

Thus, the invention has been described by reference to certain embodiments discussed above. It will be recognized that these embodiments are susceptible to various modifications and alternative forms well known to those of skill in the art.

Many modifications in addition to those described above may be made to the structures and techniques described herein without departing from the spirit and scope of the invention. Accordingly, although specific embodiments have been described, these are examples only and are not limiting upon the scope of the invention.

Furthermore, for a proper understanding of this document and in its claims, it is to be understood that the verb "to comprise" and its conjugations is used in its non-limiting sense to mean that items following the word are included, but items not specifically mentioned are not excluded. In addition, reference to an element by the indefinite article "a"

or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way

EXAMPLES

Examples 1

Preparation of Parenchynal Cellulose Composition Containing Particulate Cellulose Material Fresh sugar beet pulp obtained from Suikerunie Dinteloord (NL) was washed in a flotation washer in order to remove sand, pebbles, etc.

In a stirred tank (working volume 70 L) heated with steam), 16.7 kg of washed sugar beet pulp having a solids content of 15% DS (2.5 kg DS in the batch) was introduced and tab water was added to a total volume of 70 L. The mass was heated with steam and, once the temperature reached 50° C., 1200 gram NaOH is added. Heating was continued to reach a final temperature of 95° C. After 45 minutes at 95° C., the mixture was subjected to low shear for 30 minutes (using a Silverson BX with a slitted screen. After a total period of 3 hours at 95° C., low shear was applied again for 60 minutes (using the Silverson BX with an emulsor screen with appertures of 1.5 mm), during which the temperature was kept at approximately 95° C.

Reduction of the particles was done with a Gaulin high pressure homogenizer, operating at 150 bar (first stage; second stage was 0 bar). The mixture was homogenized 6 times. This step was performed at ambient temperature. The mixture had been allowed to cool to ambient temperature before being subjected to the high pressure homogenization treatment.

The homogenized mass was subsequently introduced in a mixing tank and heated to a temperature of 80-85° C., where after a microfiltration step was performed using a ceramic membrane with a pore size of 1.4 μm. The permeate was replaced with demineralized water. As soon as the conductivity of the retentate reached 1 mS/cm, microfiltration was discontinued. The dry solids content was between 0.5 and 1%.

This end-product was subsequently concentrated in a filter bag having pores of 100 μm to reach a dry solids content of 2%.

The material was analyzed using a Malvern Mastersizer, confirming a median (volume-weighted) major dimension of the particles contained within the material of 43.65 μm, with approximately 90% of the material (on the basis of volume) having a particle size of below 100 μm.

Example 2

Preparation of Parenchynal Cellulose Composition Containing Particulate Cellulose Material Fresh sugar beet pulp (320 kg, 24.1% ds) obtained from Suikerunie Dinteloord (NL) was washed in a flotation washer in order to remove sand, pebbles, etc.

The washed sugar beet pulp was transferred to a stirred tank (1000 L) and dilutued to a ds concentration of 8% (800 kg). Multifect pectinase FE (Genencor, 139 units/g ds) was added and the suspension was heated to 45° C. After 48 h the suspension was pressed using a membrane filterpress (TEFSA) and the resulting solid material containing the cellulose material was isolated (216 kg 12% ds).

A portion of the resulting cellulose material (20 kg) was introduced in a stirred tank (working volume 70 L) and tab water was added to a total volume of 70 L. The mixture was heated to 95° C. and subjected to low shear for a total period of 3 hours at 95° C. (using a Silverson BX with a slitted screen. Then, low shear was applied for a further 60 minutes (using the Silverson BX with an emulsor screen with appertures of 1.5 mm), during which the temperature was kept at approximately 95° C.

Reduction of the particles was done with a Gaulin high pressure homogenizer, operating at 150 bar (first stage; second stage was 0 bar). The mixture was homogenized 6 times. This step was performed at ambient temperature. The mixture had been allowed to cool to ambient temperature before being subjected to the high pressure homogenization treatment.

The homogenized mass was subsequently introduced in a mixing tank and heated to a temperature of 80-85° C., where after a microfiltration step was performed using a ceramic membrane with a pore size of 1.4 μm. The permeate was replaced with demineralized water. As soon as the conductivity of the retentate reached 1 mS/cm, microfiltration was discontinued. The dry solids content was between 0.5 and 1%.

This end-product was subsequently concentrated in a filter bag having pores of 100 μm to reach a dry solids content of 2%.

The material was analyzed using a Malvern Mastersizer, confirming a median (volume-weighted) major dimension of the particles contained within the material of 51.03 μm, with approximately 90% of the material (on the basis of volume) having a particle size of below 100 μm.

Example 3

Rheological Properties of the Parenchymal Cellulose Material

Drilling mud formulations containing the material as obtained in example 1 are prepared by mixing the following ingredients using a Hamilton Beech mixer at medium speed:

| | |
|---|---|
| Fresh water: | 350 mL |
| NaCl: | 14 g |
| NaHCO3: | 1 g |
| Standard clay: | 35 g |
| Fibers (2 wt % ds): | 2 or 3.5 g |
| Starch: | 3.5 g |

The drilling muds obtained in this manner were subjected to various tests in order to establish the suitability thereof as a well drilling fluid. More in particular, an aqueous liquid containing 2 wt. % of the cellulose based material produced in example 1, is subjected to thermal treatment by hot rolling in an Inconel autoclave for 16 hours at the temperatures indicated in the tables below. The rheology of the drilling muds before and after heat treatment was determined using a Fann 35A Rotational Viscometer at the stated rpm's.

The results of these tests are summarized in the following table

| Dosage (ppb) | Rolling Temp (° C.) | BHR | AHR | 600 | 300 | 200 | 100 | 6 | 3 | Fluid Loss (mls) |
|---|---|---|---|---|---|---|---|---|---|---|
| High Temp Tests on Sugar Beet Fibers RefST 50 +/− 2% | | | | | | | | | | |
| 2 | R.T. | X | | 80 | 69 | 64 | 57 | 34 | 30 | 14.8 |
| " | 121 | | X | 79 | 67 | 62 | 54 | 34 | 30 | 20 |
| " | 150 | | X | 63 | 49 | 43 | 36 | 21 | 18 | 46 |
| " | 175 | | X | 67 | 57 | 52 | 46 | 24 | 22 | 100 |
| 3.5 | R.T. | X | | 279 | 253 | 239 | 212 | 127 | 112 | 31.2 |
| " | 150 | | X | 151 | 134 | 121 | 104 | 62 | 54 | 46.6 |
| " | 175 | | X | 146 | 128 | 119 | 104 | 57 | 47 | 100 |

Method: Addition to Drilling Mud Formulation API 13A 4% NaCl 3.5 pbb Starch
Ppb = pounds per barrel = g/350 ml
BHR = before hot rolling
AHR = after hot rolling These results clearly confirm that the material of this invention can suitably be used to produce well drilling fluids have the desired rheological properties and, in particular, heat resistance.

The invention claimed is:

1. A parenchymal cellulose composition, comprising a particulate cellulose material comprising, by dry weight of the particulate cellulose material, (i) at least 70% cellulose, (ii) less than 10% pectin and (iii) at least 5% hemicellulose, wherein the particulate material has a volume-weighted median major particle dimension within the range of 25-75 μm, wherein at least 90%, on a volume basis, of the particles have a diameter less than 120 μm, as measured by laser light diffractometry.

2. The parenchymal cellulose composition according to claim 1, wherein the particulate material has a volume-weighted median major particle dimension within the range of 35-65 μm, as measured by laser light diffractometry.

3. The parenchymal cellulose composition according to claim 1, wherein at least 90%, on a volume basis, of the particles have a diameter less than 110 μm.

4. The parenchymal cellulose composition according to claim 1, wherein at least 90%, on a volume basis, of the particles have a diameter less than 100 μm.

5. The parenchymal cellulose composition according to claim 1, wherein the morphology of the particulate cellulose material has cellulose network structures.

6. The parenchymal cellulose composition according to claim 1, comprising less than 10 wt. % of unraveled cellulose nanofibrils.

7. A well-drilling fluid comprising, a parenchymal cellulose composition according to claim 1 dispersed in an aqueous medium.

8. The well-drilling fluid according to claim 7, further comprising at least one well drilling fluid additive selected from the group consisting of thinning and dispersing agents, lubricants, shale stabilizing agents, pH control agents, filtrate reducing agents, fluid loss agents, corrosion inhibitors, oxygen scavengers, and weighting agents.

9. The parenchymal cellulose composition according to claim 1, wherein the particulate cellulose material has been subjected to high pressure homogenization.

10. A method of preparing a parenchymal cellulose composition according to claim 1, the method comprising:
    (a) subjecting parenchymal cell-containing vegetable pulp to chemical and/or enzymatic treatment resulting in partial degradation and/or extraction of pectin and hemicellulose, wherein the mixture may be homogenized once or several times by applying low shear force during and/or after said chemical and/or enzymatic treatment;
    (b) subjecting the material resulting from step (a) to a high shear process, wherein the particle size of the cellulose material is reduced so as to yield a particulate material having a volume-weighted median major dimension within the range of 25-75 μm, wherein at least 90%, on a volume basis, of the particles have a diameter less than 120 μm, as measured by laser light diffractometry; and
    (c) removing liquid from the mass obtained in step (b).

11. The method according to claim 10, wherein the vegetable pulp is sugar beet pulp.

12. The method according to claim 10, wherein the chemical treatment comprises:
    (i) mixing the parenchymal cell containing vegetable pulp with a 0.1-1.0 M alkaline metal hydroxide; and
    (ii) heating the mixture of parenchymal cell containing vegetable pulp and alkaline metal hydroxide to a temperature within the range of 80-120° C. for a period of at least 10 minutes.

13. The method according to claim 12, comprising mixing the parenchymal cell containing vegetable pulp with a 0.3-0.7 M alkaline metal hydroxide.

14. The method according to claim 10, wherein the alkaline metal hydroxide is sodium hydroxide.

15. The method according to claim 12, wherein the mixture is heated to a temperature between 90-100° C.

16. The method according to claim 10, wherein the high sheer process comprises a high pressure homogenization treatment.

17. The method according to claim 10, wherein step (c) comprises pressing of the composition, while allowing the composition to expand laterally, to reduce the water content of the composition.

* * * * *